United States Patent [19]
Weston

[11] Patent Number: 6,135,979
[45] Date of Patent: Oct. 24, 2000

[54] SPRING-POWERED DISPENSING DEVICE FOR MEDICAL PURPOSES

[75] Inventor: Terence Edward Weston, Eye, United Kingdom

[73] Assignee: Weston Medical Limited, Eye, United Kingdom

[21] Appl. No.: 09/178,991

[22] Filed: Oct. 9, 1998

Related U.S. Application Data

[63] Continuation of application No. PCT/GB97/00812, Mar. 21, 1997.

[30] Foreign Application Priority Data

Apr. 11, 1996 [GB] United Kingdom ................... 9607549

[51] Int. Cl.⁷ .................................................... A61M 5/30
[52] U.S. Cl. .............................................. 604/68; 604/134
[58] Field of Search .................................. 604/68, 69, 70, 604/71, 131–135, 140, 143, 141

[56] References Cited

U.S. PATENT DOCUMENTS

| | | | |
|---|---|---|---|
| 2,653,602 | 9/1953 | Smooth | 128/173 |
| 2,680,439 | 9/1954 | Sutermeister | 128/173 |
| 3,217,712 | 11/1965 | Blumenstein | 128/216 |
| 3,945,383 | 3/1976 | Bennett et al. | 128/272 |
| 4,351,692 | 9/1982 | Ouellette | 156/443 |
| 4,902,279 | 2/1990 | Schmidtz et al. | 604/134 |
| 5,026,349 | 6/1991 | Schmitz et al. | 604/134 |
| 5,865,795 | 2/1999 | Schiff et al. | 604/70 |
| 5,891,086 | 4/1999 | Weston | 604/68 X |

FOREIGN PATENT DOCUMENTS

| | | | |
|---|---|---|---|
| WO 93/03779 | 3/1993 | European Pat. Off. | A61M 5/30 |
| WO 94/11041 | 5/1994 | European Pat. Off. | A61M 5/20 |
| WO 95/03844 | 2/1995 | European Pat. Off. | A61M 5/30 |
| WO 96/28202 | 9/1996 | European Pat. Off. | A61M 5/30 |
| 824357 | 2/1938 | France. | |
| 518 102 | 3/1972 | Switzerland | A61M 5/20 |

*Primary Examiner*—John D. Yasko
*Attorney, Agent, or Firm*—Darby & Darby

[57] ABSTRACT

A dispensing device, such as a needleless injector, comprising a spring, which provides an energy store, and a dispensing member movable, to effect a dispensing, under the force of the spring. A latch has a first position in which it restrains movement of the dispensing member and a second position in which it permits such movement. A trigger is operable by the user for moving the latch from the first position to the second position. A safety mechanism, preferably in the form of an appropriately shaped slot in the dispensing member, is effective before the device has been completely assembled to prevent movement of the latch to the second position.

15 Claims, 2 Drawing Sheets ically in the range 5.5 MPa (800 psi) to 20.7 MPa (3000 psi).
SPRING-POWERED DISPENSING DEVICE FOR MEDICAL PURPOSES This is a continuation of international Application PCT/GB97/00812, filed Mar. 21, 1997.

FIELD OF THE INVENTION

This invention relates to a dispensing device which employs a spring to urge a dispensing member to disperse, for example, a dose of liquid, powder, or a pellet. The spring may, for example, be a mechanical spring, such as of metal, or a compressed gas spring, such as of compressed air.

BACKGROUND OF THE INVENTION

One example of such a dispensing device is a needleless injector. Needleless injectors of various types are described in, inter alia, International Patent Publications Nos. WO 93/03779 and WO 95/03844, which are in the name of the present applicant. The present invention will be described in detail with reference to a needleless injector, but it is to be understood that it applies to other types of spring powered dispensing device also.

In a spring powered needleless injector of the type described in the above International Patent Publications, the spring continuously exerts a force on a dispensing member, prior to use, and restraining means are provided for preventing the dispensing member moving under the force of the spring. The needleless injector is fired by, in effect, moving the injector into a condition in which the restraining means no longer have a restraining effect, thus permitting the dispensing member to move.

There is, however, a potential problem is assembling such devices, in that if the device is to be easily operable by the user, it may be easy, or at least possible, for the device to be accidentally fired during the process of manufacture. This is not only wasteful, but also poses a safety hazard to the personnel involved. It is an object of the present invention to provide means for overcoming this problem.

SUMMARY OF THE INVENTION

According to the present invention there is provided a device for dispensing a material or article, which comprises a spring, which provides an energy store, a dispensing member movable, to effect dispensing, under the force of the spring, latch means having a first position in which it restrains movement of the dispensing member and a second position in which it permits such movement, trigger means operable by the user for moving the latch means from said first position to said second position, and a safety mechanism effective before the device has been completely assembled to prevent movement of the latch means to the second portion.

In a preferred embodiment of the invention, described in more detail below, the safety mechanism is incorporated into the latch member, which then has a safety position, in which it cannot be moved to its second position by the trigger means, and a non-safety position, in which it can be so moved.

BRIEF DESCRIPTION OF THE DRAWINGS

The invention will now be further described with reference to the accompanying drawings, in which.

DETAILED DESCRIPTION OF THE INVENTION

Figure 1:
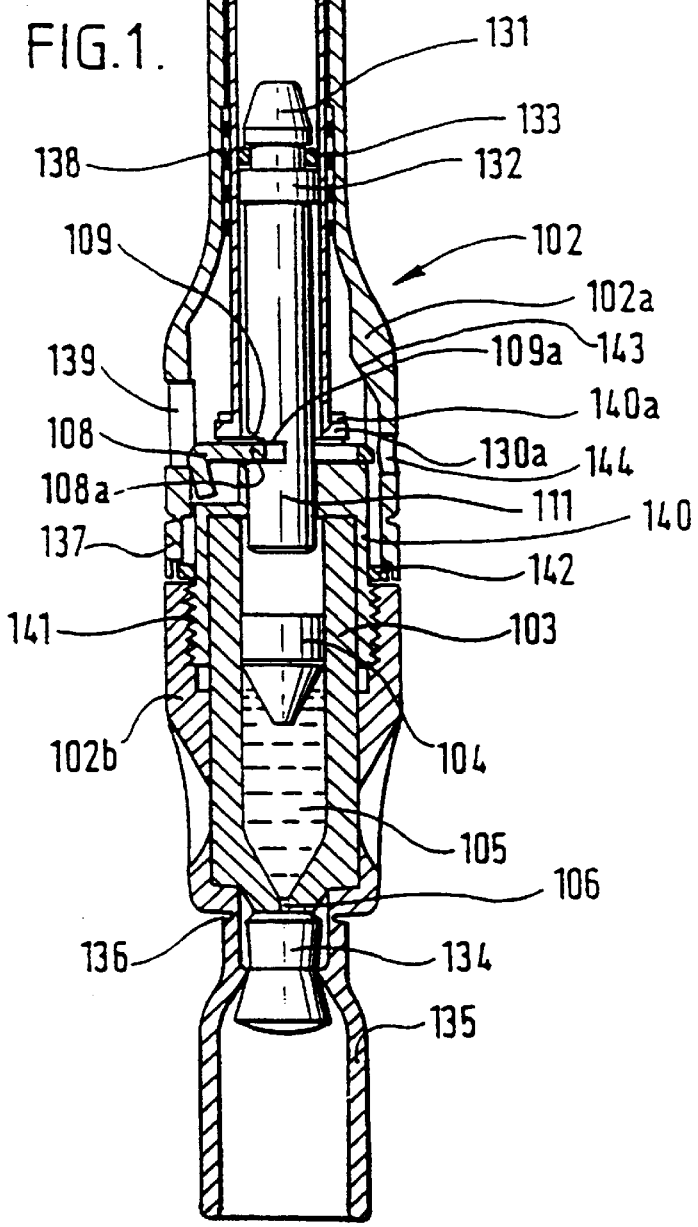
FIG. 1 is a longitudinal section through an embodiment of a needleless injector according to the invention, and showing the injector prior to use, and with its latch in its safety position.
Figure 1A:
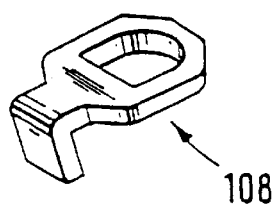
FIG. 1a shows on a larger scale the latch used in FIG. 1.

In the embodiment of FIG. 1, the injection force is provided by a compressed gas spring. This is in the form of a cylinder 130 which is closed at its upper end and which contains gas, typically air, under a pressure which is typically in the range 5.5 MPa (800 psi) to 20.7 MPa (3000 psi). The cylinder houses a ram 111. The end of the ram 111 has a frustoconical portion 131 and a flange 132 between which is situated an O-ring seal 133. Prior to use, the ram 111 is held in the illustrated position by a latch 108 engaging in a groove in the ram, the upper surface of the groove forming a cam surface 109. The latch 108 is shown on a larger scale in FIG. 1a. In the position shown in FIG. 1 the latch is unable to move leftwards, because it bears against the inner wall of a sleeve 102.

The lower end of the cylinder 130 has an outwardly directed flange 130a, which enables the cylinder to be held by crimping the flange 130a beneath an outwardly directed flange 140a at the upper end of a coupling 140. The sleeve 102 is formed of an upper sleeve portion 102a within which the cylinder is situated, and a lower sleeve portion 102b. The sleeve portion 102b is connected to the coupling by the interengaging screw threads 141 formed on the inner and outer walls of the sleeve portion 102b and coupling 140 respectively.

The injector contains a medicament cartridge 103 which has a piston 104 slidingly and sealingly located therein, in contact with medicament 105. As considered from the upper end of FIG. 1, the piston may comprise a cylindrical portion, a larger diameter cylindrical sealing portion, and a frustoconical portion, for example as seen in FIG. 1 of PCT/GB96/00551 referred to below. The cartridge 103 has a discharge orifice 106. The orifice 106 is sealed by a resilient seal 134 which is held in place by a seal carrier 135. The seal carrier 135 is connected to the lower sleeve portion 102b by a frangible joint 136.

As a precaution against accidental firing, a tear-off band 137 is provided as the lower part of the upper sleeve portion 102a. The lower edge of the tear-off band 137 bears against a ring 142 which is bonded to the exterior surface of the coupling 140 or (not shown) formed integrally therewith. The function of the ring is to prevent downward movement of the sleeve portion 102a relative to the coupling 140, for so long as the tear-off band 137 is present. Accordingly, the ring 142 need not extend completely around the periphery of the coupling, and could be replaced by one or more separate elements.

An annular space 138 is formed in the inside wall of the sleeve 102, where the sleeve is adjacent the cylinder 130, and the space is filled with a damping grease (indicated diagrammatically by a succession of black bands), so that the grease is in intimate contact both with the sleeve 102 and the cylinder 130. It should be noted that although a defined annular space is convenient from the point of view of providing a particular location for the grease, it could be omitted and the grease simply smeared over all or part of the outside of cylinder 130 and/or inside of sleeve 102.

When the embodiment of FIG. 1 is to be operated, the user snaps off the seal carrier 135 at the frangible joint 136, which takes the seal 134 with it and exposes the orifice 106. The user then removes the tear-off band 137, and grasping the upper part of the sleeve 102 urges the orifice against the substrate (e.g. the user's own skin) which is to be injected. This moves the upper sleeve portion 102a downwardly, with respect to the lower sleeve portion 102b. This brings aperture 139 in the wall of the upper sleeve portion 102a into alignment with the latch 108, which is thus able to move sideways into the aperture under the influence of the force of the gas within the cylinder 130 acting on the latch via the cam surface 109 formed in the ram 111. The injector is thus caused to fire. As a precaution, in case the latch fails to move under the influence of the cam surface 109, an auxiliary cam surface 143 is provided on the inside of the sleeve portion 102a. The resulting recoil is damped by the damping grease.

By way of example only, the following are typical measurements for the embodiment of FIG. 1:

| | |
|---|---|
| Diametrical clearance between gas cylinder outside diameter and sliding sleeve inside diameter | 0.05 mm |
| Area of shear (i.e. cross section of grease) approximately | 375 mm² |
| Viscosity of grease | 2.2 Kilopoise |
| Momentum of ram at impact | 0.06 kg · m/s |
| Mass of sleeve portion 102a | 1.3 g |
| Mass of ram | 2.5 g |
| Impact gap between ram and piston | 4 mm |
| Gas pressure | 6.2 MPa |
| Bore of gas cylinder | 5.0 mm |

While grease has been discussed as a preferred damping medium, similar results may be obtained by using air or oil damping devices—usually a cylinder and piston combination, i.e. a so-called "dashpot", wherein a fluid substance is caused to flow through a restriction, thereby to resist motion. Other viscous damping devices employ a vane, or a plurality of vanes, spinning in a damping medium, for example air, and these may be used if appropriate to the particular application. The effect and purpose of the damping grease is discussed in more detail in our copending International Application No. PCT/GB96/00551.

It will be appreciated that it is important that needleless injectors, or indeed any injectors with power stored in them, should not be able to fire prematurely. Once the above described device has been assembled this is achieved by the presence of the tear band 137, since until that is removed the device cannot fire. However, there is a potential problem in assembling the device, in that the penultimate component to be assembled is the upper sleeve portion 102a, which carries the tear band 137, (the last component to be assembled is the cartridge 103) and until the sleeve portion 102a is in place accidental firing is possible.

Accidental firing during the assembly process is a real possibility. Firstly, immediately prior to installation of the upper sleeve portion 102a there is a stage in which the partially assembled device has a period of quarantine to check for gas leaks. Secondly, during installation of the upper sleeve portion 102a the device will be subjected to numerous forces and vibration arising from the assembly equipment. Even after installation of the upper sleeve portion 102a, the assembly stresses arising as the cartridge is installed may be sufficient to cause accidental firing, despite the presence of the tear band 137.

To deal with this problem the device has a safety mechanism. In the illustrated embodiment this is provided by forming the slot in the ram not only with the cam surface 109 but also with a locking surface 109a which extends perpendicular to the axis of the ram and is located radially inwardly of the cam surface 109. To enable the combination of cam surface 109 and locking surface 109a to be used in the intended manner, the upper sleeve portion 102a is provided with an opening 144 which extends therethrough at a location which, prior to the device being fired, is aligned with the end of the latch 108 remote from the slot in the ram.

Figure 2A:
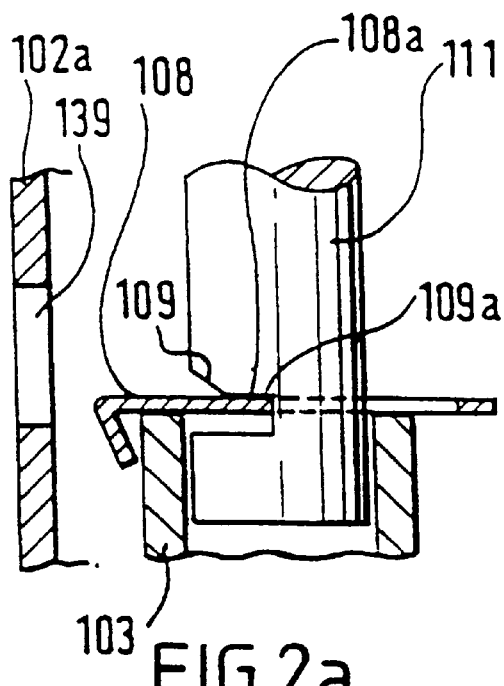
FIGS. 2a, 2b and 2c show diagrammatically part of the embodiment of FIGS. 1 and 1a, in three successive stages, namely with the latch in is safety position, with the latch in its non-safety position prior to firing, and with the latch in its position during firing.
Figure 2B:
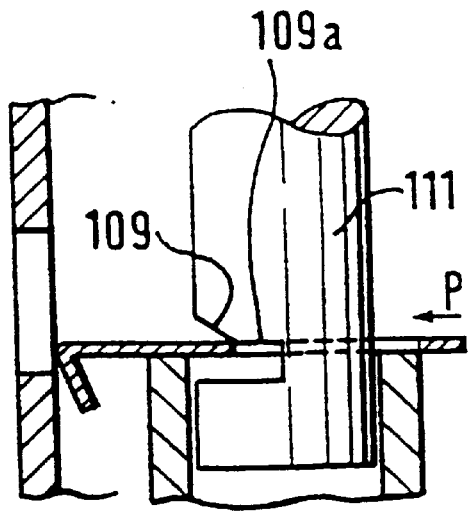
Figure 2C:
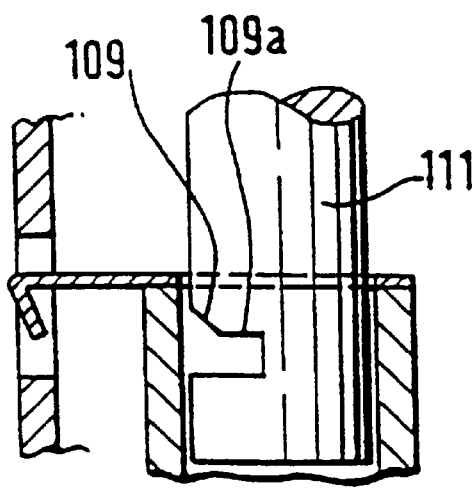

The way in which the safety mechanism operates can be seen from FIGS. 2a, 2b and 2c. When the latch and ram are initially assembled with one another, the latch occupies the position shown in FIG. 2a, which is a safety position. Here, the ram-engaging latch portion 108a is acted on by the locking system 109a. Friction forces ensure that the latch remains engaged with the locking surface; typically the ram exerts a force of at least 200N, so the latch is held in a vice-like grip.

Once the device has been assembled, preferably completely, and at least to the extent of the upper sleeve portion 102a being in place, it is cocked by inserting a tool through the opening 144 to push the latch in the direction of the arrow P in FIG. 2 into the position shown in FIG. 2b (and in FIG. 1). In this position the ram-engaging latch portion 108a is in contact with the radially inner end of the cam surface 109. Accordingly, when the device is actuated as described above it is able to fire, and the latch moves to the position shown in FIG. 2c.

What is claimed is:

1. An injector for dispensing a liquid, which comprises a spring, which provides an energy store, a dispensing member movable, to effect dispensing, under the force of the spring, latch means having a first position in which it restrains movements of the dispensing member and a second position in which it permits such movement, trigger means operable by the user for causing the latch means to move from said first position to said second position, and a safety mechanism effective before the device has been completely assembled to prevent movement of the latch means to said second position, wherein the safety mechanism is provided by a slot extending into the dispensing member from an exterior surface thereof, the slot being defined in part by a pair of latch-engaging surfaces, the latch means having a safety position in which it cannot be caused to move to the said second position by operation of the trigger, in which it engages one of the surfaces, and engaging the other of the surfaces when in its said first position.

2. An injector according to claim 1, wherein the said one surface is substantially perpendicular to the intended direction of movement of the dispensing member, and the said other surface is inclined to the said direction of movement so that the movement of the dispensing member in the said direction exerts a force on the latch means, when the latch means is in its said first position, urging it towards its said second position.

3. An injector according to claim 1, having an outer casing surrounding the dispensing member and latch means, the outer casing having an aperture therethrough in the region of the latch means, the aperture providing access to permit insertion of a tool into the interior of the outer casing to move the latch means from its safety position to its said first position.

4. An injector according to claim 1, which is a needleless injector.

5. An injector according to claim 4, comprising a chamber containing a liquid to be injected and provided with an outlet orifice at one end thereof and a piston movable in the chamber to expel the said liquid through the outlet orifice, the dispensing member being spaced from the piston when the latch means is in its said first position and striking the piston to effect movement thereof when the latch means is moved to its said second position.

6. A device according to claim 1, wherein the spring is a gas spring.

7. A device according to any claim 1, wherein the spring is a mechanical spring.

8. A device for dispensing a material or article, which comprises a spring, which provides an energy store, a dispensing member movable, to effect dispensing, under the force of the spring, latch means having a first position in which it restrains movement of the dispensing member and a second position in which it permits such movement, trigger means operable by the user for causing the latch means to move from said first position to said second position, and a safety mechanism effective before the device has been completely assembled to prevent movement of the latch means to said second position, said safety mechanism being provided by said latch means having a safety position in which is cannot be caused to move to said second position by the operation of the trigger, and wherein the dispensing member has a pair of latch-engaging surfaces therein, the latch means engaging one of the surfaces when in its safety position, and the other of its surfaces when in said first position.

9. A device according to claim 8, wherein the dispensing member has a slot extending into it from an exterior surface thereof, the slot being defined in part by the said pair of surfaces.

10. A device according to claim 8, wherein the said one surface is substantially perpendicular to the intended direction of movement of the dispensing member, and the said other surface is inclined to the said direction of movement so that the movement of the dispensing member in the said direction exerts a force on the latch means, when the latch means is in its said first position, urging it towards its said second position.

11. A device for dispensing a material or article, which comprises a spring, which provides an energy store, a dispensing member movable, to effect dispensing, under the force of the spring, latch means having a first position in which it restrains movement of the dispensing member and a second position in which it permits such movement, trigger means operable by the user for causing the latch means to move from said first position to said second position, and a safety mechanism effective before the device has been completely assembled to prevent movement of the latch means to said second position, said safety mechanism being provided by said latch means having a safety position in which is cannot be caused to move to said second position by the operation of the trigger, and an outer casing surrounding the dispensing member and latch means, the outer casing having an aperture therethrough in the region of the latch means, the aperture providing access to permit insertion of a tool into the interior of the outer casing to move the latch means from its safety position to its said first position.

12. A device according to claim 8, which is in the form of a needleless injector.

13. A device for dispensing a material or article, which comprises a spring, which provides an energy store, a dispensing member movable, to effect dispensing, under the force of the spring, latch means having a first position in which it restrains movement of the dispensing member and a second position in which is permits such movement, trigger means operable by the user for causing the latch means to move from said first position to said second position, and a safety mechanism effective before the device has been completely assembled to prevent movement of the latch means to said second position, said device further comprising a chamber containing a liquid to be injected and provided with an outlet orifice at one end thereof and a piston movable in the chamber to expel the said liquid through the outlet orifice, the dispensing member being spaced from the piston when the latch means is in its first position and striking the piston to effect movement thereof when the latch means is moved to its second position.

14. A device according to claim 8, wherein the spring is a gas spring.

15. A device according to claim 8, wherein the spring is a mechanical spring.

* * * * *